(12) United States Patent
Dodabalapur et al.

(10) Patent No.: US 6,661,299 B2
(45) Date of Patent: Dec. 9, 2003

(54) ODOR SENSOR WITH ORGANIC TRANSISTOR CIRCUITRY

(75) Inventors: Ananth Dodabalapur, Millington, NJ (US); Alan Gelperin, Princeton, NJ (US); Howard Edan Katz, Summit, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 220 days.

(21) Appl. No.: 09/793,050

(22) Filed: Feb. 26, 2001

(65) Prior Publication Data

US 2002/0117693 A1 Aug. 29, 2002

(51) Int. Cl.⁷ .............................. H03B 1/00; H01L 23/58
(52) U.S. Cl. .............................. 331/57; 331/74; 422/90; 73/23.34; 73/31.06; 73/23.21; 324/71.5; 257/252; 257/253
(58) Field of Search .............................. 73/23.34, 31.06, 73/23.21; 324/71.5; 422/90, 74; 331/57; 257/252, 253

(56) References Cited

U.S. PATENT DOCUMENTS

| 4,344,293 A | * | 8/1982 | Fujiwara et al. | ............... 62/126 |
| 6,484,559 B2 | * | 11/2002 | Dodabalapur et al. | ..... 73/23.34 |

* cited by examiner

*Primary Examiner*—Arnold Kinkead

(57) ABSTRACT

Circuits include at least one-odor sensitive organic transistor having a conduction channel whose conductivity changes in response to certain odors. The organic transistors are interconnected to increase their response to selected odor signals. The organic transistors may be interconnected to form a ring oscillator whose frequency of oscillation changes in response to an odor signal and in which the alternating signal applied to the gate electrodes of the organic transistors enhances their recovery and reduces their drift.

27 Claims, 13 Drawing Sheets

P-TYPE OFET

P-TYPE FET

N-TYPE OFET

N-TYPE FET

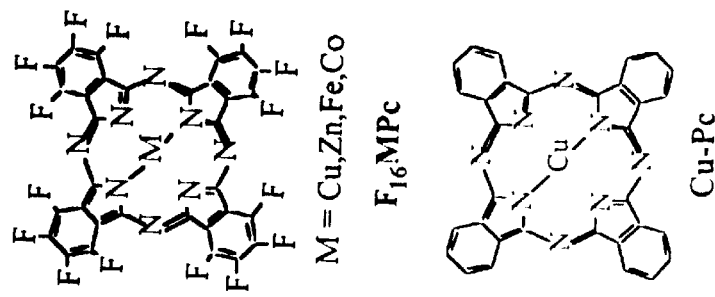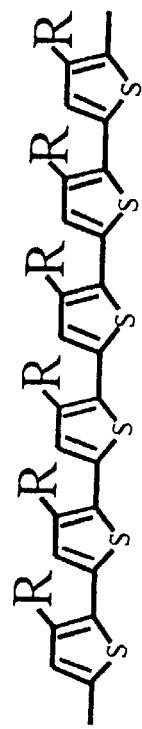
FIG. 13

US 6,661,299 B2

ODOR SENSOR WITH ORGANIC TRANSISTOR CIRCUITRY

BACKGROUND OF THE INVENTION

This invention relates to circuitry employing organic transistors and, in particular, organic field effect transistors (OFETs) to detect chemical odors/vapors/gases (analytes).

Many different types of OFETs are known. By way of example, FIG. 1 shows the structure of an OFET 10 having a semiconductor body region 12 with a source electrode 14 and a drain electrode 16 defining the ends of a conduction channel through the semiconductor body 12. The OFET 10 also includes an insulator layer 18 and a gate (control) electrode 20 to which a voltage may be applied to control the conductivity of the semiconductor body region (i.e., the conduction channel). The OFET of FIG. 1 is manufactured to have organic material in its semiconductor body region 12 that can absorb analytes and which, in response to the absorbed analytes, changes the conductivity characteristics of the conduction channel. As illustrated in FIG. 1, analytes (vapors/odors/gases) may flow over the OFET for a period of time. Ensuing changes in the conductivity of the OFET may be measured as shown in FIG. 1A by sensing the current ($I_d$).

In known circuitry, the OFETs have been used as discrete devices. As shown in FIG. 1A, the source of an OFET may be connected to a first point of operating potential (e.g., VDD) and its drain may be connected via a load resistor RL to a second point of operating potential (e.g., ground potential). The gate of the OFET may be biased via resistors R1 and R2 to produce a desired operating direct current (d.c.) bias level within the source-drain (i.e., conduction) path of the OFET. The OFET may then be subjected to a flow of analytes which causes its conductivity to change. The corresponding change in conductivity of the OFET is then detectable by a circuit connected to the drain and/or the source of the OFET.

A problem with known OFETs is that their sensitivity to the analytes is relatively low. Also, known OFETs are subject to drift and threshold shift as a function of time, as shown in FIG. 2A and FIG. 2B, respectively. In FIGS. 2A and 2B, it is seen that, for a fixed bias condition, source-to-drain current ($I_d$) of an OFET changes (e.g., decreases) as a function of time. This is the case when there is no signal input (i.e., no odor), as illustrated by waveform A of FIG. 2A and waveform portion C in FIG. 2B. This is also the case following the application of an odor to the OFET, as illustrated in waveform B of FIG. 2A and in waveform portion D in FIG. 2B. That is, for a fixed bias condition, the current through the conduction path of the OFET changes (drifts) as a function of time. OFETs may also be subjected to hysteresis and offsets. As a result of these characteristics, it is difficult to use OFETs in known discrete circuits to differentiate an input signal from background conditions and to determine or measure the full extent of the input signal.

SUMMARY

Problems associated with the characteristics of OFETs, such as time-related drift, detract from their use as sensors and amplifiers of their sensed signals when the OFETs are used as discrete devices. Applicants recognized that OFETs should be incorporated in circuits specifically designed to overcome and/or cancel the problems associated with certain characteristics of OFETs such as their drift, threshold shift and hysteresis.

Circuits of various embodiments include at least one odor-sensitive organic transistor having a conduction channel whose conductivity changes in response to certain ambient odors.

In one embodiment, organic transistors are interconnected to increase their response to selected odor signals and such that the recovery of the organic transistors is enhanced and their drift is reduced. In a particular embodiment, the organic transistors are interconnected to form a ring oscillator whose frequency of oscillation changes sharply in response to an odor signal and in which the alternating signal applied to the gate electrodes of the organic transistors enhances their recovery and reduces their drift.

BRIEF DESCRIPTION OF THE DRAWINGS

In the accompanying drawing, like reference characters denote like components.

FIG. 12 is a cross section of an OFET suitable for use in circuits embodying the invention;

FIG. 13 is a drawing of various molecular structures of several materials used to make OFETs.

DETAILED DESCRIPTION OF THE EMBODIMENTS

In the discussion to follow, reference is made to organic field effect transistors (OFETs) which may be used to sense odors, vapors, chemicals and/or gases (analytes). These terms are used interchangeably and are intended to include each other in the specification and in the claims appended hereto. OFETs have been described in the literature and the teachings of these references as to the manufacture of these transistors and their reported characteristics are incorporated herein by reference. In the discussion to follow references to OFETs will also include organic thin film transistors (OTFTs) and any device having similar characteristics.

Figure 3A:
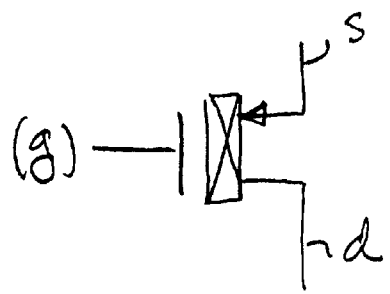
FIGS. 3A and 3B are the symbolic representation of P-type OFETs and P-type FETs, respectively, used in this application.
Figure 3B:
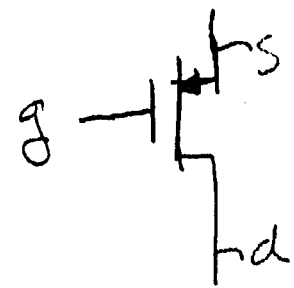
Figure 4A:
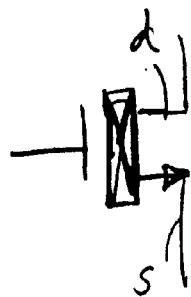
FIGS. 4A and 4B are the symbolic representation of N-type OFETs and N-type FETs, respectively, used in this application.
Figure 4B:
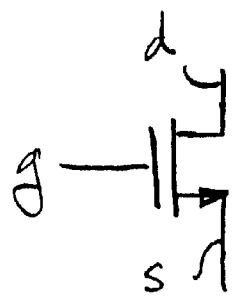

To better understand the discussion to follow and the drawings appended hereto, certain characteristics of OFETs will first be discussed. OFETs (or OTFTs) may be of N-conductivity type or P-conductivity type. To more easily differentiate the OFETs from known field effect transistors (FETs), the following symbology will be used in the appended drawings: (a) P-type OFETs will be shown as illustrated in FIG. 3A; (b) P-type FETs will be shown as illustrated in FIG. 3B; (c) N-type OFETs will be identified as shown in FIG. 4A; and (d) N-type FETs will be identified as shown in FIG. 4B. The drawings for the OFETs include a rectangular box, with an X through the box, indicative of the semiconductor body with source and drain electrodes attached to the semiconductor body representing the ends of a conduction path (or channel) through the semiconductor body. The semiconductor body is electrically insulated from a gate (control) electrode, g, to which a bias voltage or a signal may be applied to control the conductivity of the semiconductor body. A P-type OFET is shown with an arrow pointing towards the body of the OFET and an N-type OFET is shown with an arrow pointing away from the body of the OFET. The semiconductor body defines the conduction path and the OFET includes source and drain electrodes defining the ends of the conduction path. OFETs, like FETs, are generally bi-directional conducting devices. Therefore: (a) the source of a P-type OFET or of a P-FET is defined as the one of the two electrodes connected to the semiconductor body whose potential is more positive than the other (drain) electrode; and (b) the source of an N-type OFET or of an N-FET is defined as the one of the two electrodes connected to the semiconductor body whose potential is less positive than the other (drain) electrode.

As noted above, OFETs are typically subject to several problems:

a) low sensitivity; (b) drift; (c) hysteresis; and (d) variation of their threshold voltage ($V_T$) as a function of time.

The various embodiments are directed to circuits that use OFETs but are configured to reduce or compensate for the problems associated with low sensitivity, drift, threshold shift and hysteresis.

Figure 5:
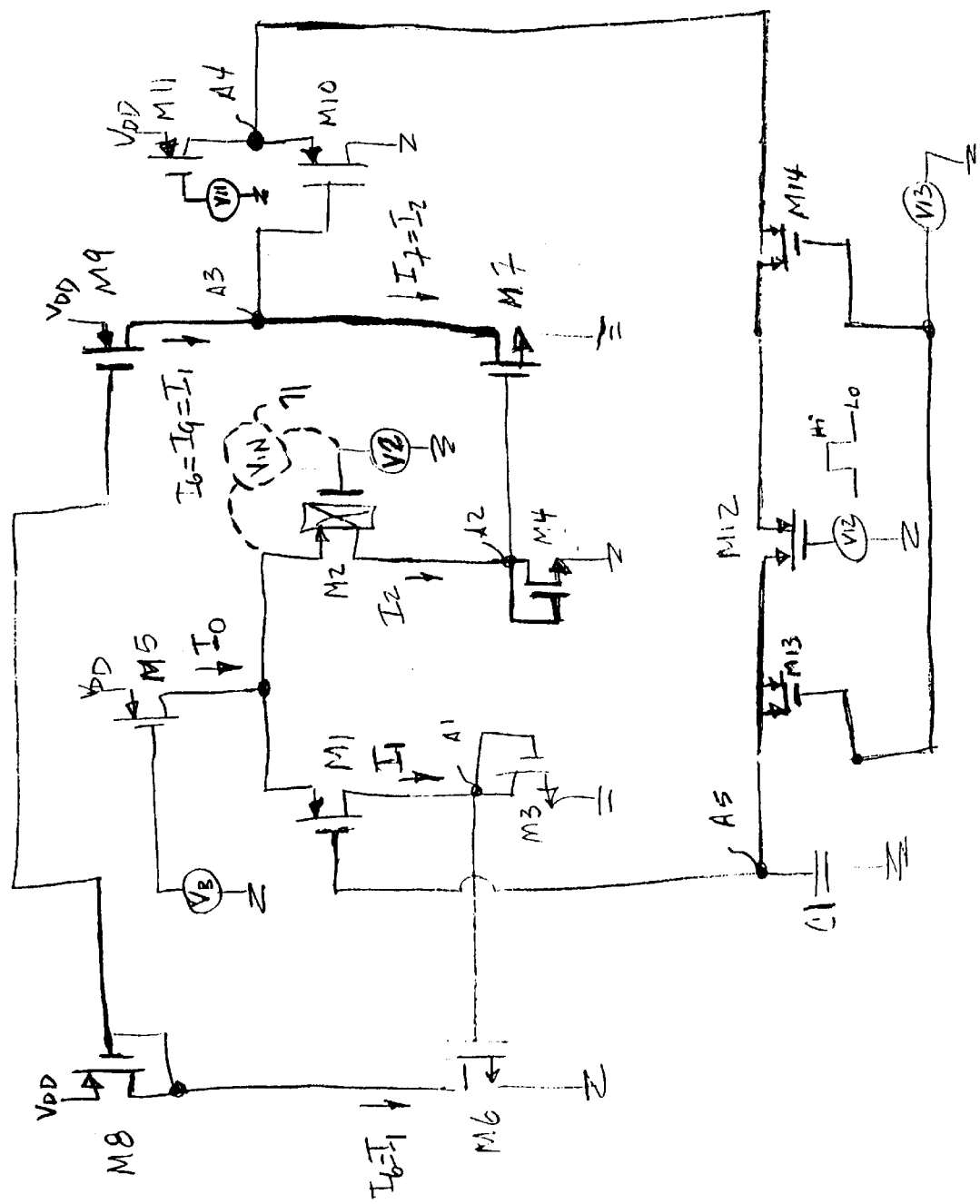
FIG. 5 is a schematic diagram of an OFET-differential amplifier combination embodiment the invention.

FIG. 5 illustrates the use of an organic transistor, OFET M2, as a sensor of odors and as an amplifier of the signal sensed. In the discussion to follow, when an odor flows over an OFET and the OFET is turned-on and/or biased into conduction, the OFET may be said to be "sensing" or "sniffing" the odor and to be in a sensing or sniffing mode. OFET M2 forms part of the input stage of a differential amplifier. The amplifier includes selectively enabled adaptive feedback circuitry, which enables the background, drift and threshold shift conditions to be effectively subtracted from the amplified output signal. When the amplifier circuit is in a standby non-sensing mode (i.e., not sensing or sniffing any odors, gases, chemical vapors etc.) negative feedback is used to cancel any drift or threshold shift due to OFET M2. When the circuit is in a sensing mode (i.e., "sniffing") the feedback loop is opened with the circuit biased in a high gain state so it can respond quickly and with high gain to an input signal.

In the circuit of FIG. 5, transistor M2 is an odor-sensitive P-type OFET. For ease of illustration the other transistors used in the circuit are non-odor sensitive FETs or OFETs. Transistors M1, M2, and M5 form the input stage of a differential amplifier, with the source electrodes of M1 and M2 being connected to the drain of M5. Thus, M1 and M2 compete for the current from current-source M5. The source electrode of M5 is connected to a point of fixed operating potential (i.e., VDD) and a bias voltage $V_B$ is applied to the gate of M5 causing a constant current, Io, to flow through the conduction path of M5. The current Io is equal to the sum of the current I1 through the conduction path of M1 and the current I2 through the conduction path of M2; that is, Io=I1+I2. The value of the current flowing through the conduction paths of M1 and M2 is a function of their relative gate voltages. The lower the gate voltage of M1 with respect to M2, the greater is the fraction of the current Io that flows through it; similarly for M2. The drain of M1 is connected to node A1 and the drain of M2 is connected to node A2.

The current I1 flowing into node A1 is mirrored via a current mirror circuit comprised of transistors M3 and M6 to produce a current I6 flowing through the conduction paths of transistors M6 and M8. For ease of illustration, assume that the current current I6 which is equal to the current I8 is also equal to the current I1 ; i.e., I6=I8=I1. The current through M8 is then mirrored via a current mirror comprised of transistors M8 and M9 to cause a current I9 to flow through the conduction path of M9 into node A3. The sources of M8 and M9 are connected to VDD volts and their gates are connected in common to the drains of M8 and M6. When M8 and M9 have similar geometries, their drain currents will be substantially equal for the same gate-source bias conditions. In that case, the current I9 flowing into node A3 is equal to I6 which is, in turn, equal to I1; i.e., I1=I6=I9.

The drain current I2 through M2 flows into node A2 and is mirrored via the current mirror transistor combination of M4 and M7. The sources of M4 and M7 are connected to ground potential and the gate of M7 is connected to the gate and drain of M4. When M4 and M7 are of similar geometries their drain currents will be substantially the same for like gate-source bias conditions. Thus, M4 and M7 function as a current mirror to produce a current I7 through the conduction path of M7 which is drawn out of node A3. In that case, the current I7 is equal to the current I2. For the above conditions, if I1 is equal to I2, the current I9 flowing into node A3 is equal to the current I7 flowing out of node A3. Where M9 and M7 have essentially equal impedances for the corresponding bias condition, the voltage at node A3 will be substantially equal to VDD/2 when I1 is equal to I2. It should also be appreciated that, since M7 and M9 are effectively high impedance current sources, a small difference between the currents I9 and I7 results in a large voltage differential at node A3. Thus, the circuit has a very large open circuit (i.e., when there is no feedback) voltage gain.

Thus, the pair of currents I1 and I2 are mirrored via the current mirrors formed by M3–M6, M4–M7, and M8–M9 and compared with each other to generate an output voltage at node A3. If the current through M2 exceeds that through M1, then the node voltage A3 is driven to a value near ground. If the current through M1 exceeds that through M2, then the node voltage A3 is driven to a value near VDD volts. Thus, transistors M1–M9 implement a wide-output range differential amplifier with inputs given by the gate voltages of M1 and M2 and an output given by the voltage at node A3.

The gate of OFET M2 is connected to a relatively constant bias voltage source V2. To better illustrate the operation of the circuit and the role of M2 as a sensor, an input signal source 71 is shown connected between the source and gate of M2. The source 71 and its connections are shown with dashed lines since this source is internal to OFET M2. The Vin source 71 depicts the equivalent input signal due to a mobility or threshold voltage change in transistor M2 when an odor is "puffed" onto (i.e., applied to) it. An odor "puffed" onto transistor M2 is equivalent to the application of an input signal to its gate. When an odor to be sensed is applied to M2, the feedback loop is opened (i.e., P-type transistor M12 is turned off by driving voltage V12 to an active high state). Transistor M2 is the only odor sensitive transistor in the circuit of FIG. 5.

The gate of transistor M1 is connected to the output (i.e., node A5) of a low pass filter whose input is connected to the output (i.e., node A3) of the differential amplifier to provide a negative feedback configuration. That is, output node A3 of the amplifier is applied to the input of a source follower stage (i.e., the gate of M10) comprised of transistors M10 and M11. The source of M11 is at VDD volts and a bias voltage V11 is applied to the gate of M11 to establish a current through M11 and M10. The source of M10 is connected to the drain of M11 at an output node A4 and the drain of M10 is returned to ground potential. The conduction path of a transistor switch M12 is connected between node A4 and node A5 which is connected to the gate of M1. A capacitor C1 is connected between the gate of M1 and ground potential. The low pass filter is implemented with transistors M10, M11 and capacitor C1. When transistor M12 is turned on closing the feedback loop (i.e. the circuit is not "sniffing"), the output at node A4 of the source follower is connected to capacitor C1 (via the low "ON" impedance of M12) such that transistors M10, M11 and capacitor C1 implement a weakly nonlinear low pass filter. The time constant of the low pass filter may be controlled by altering V11 or the value of the capacitance of C1 or both.

When the feedback loop is closed (i.e., M12 is turned on), any drift or change in the conductivity of M12 is effectively cancelled because a conductivity change of M2 causes a corresponding change in I2. The change in I2 then causes a corresponding change in the voltages at nodes A3 and A4. The change at A4 is then applied via M12 to the gate of M1 with a magnitude and polarity to cause a change in I1 which cancels or offsets the change in I2 caused by M2 (i.e., negative feedback tends to cause I1 to equal I2). Thus, when the negative feedback loop is closed, the gate voltage of M1 adapts to compensate (or cancel) for long-term, time dependent, changes between the threshold or mobility of transistors M1 and M2 and automatically keeps the differential amplifier output at its balanced midpoint.

As noted above, when the circuit is not sniffing, the negative feedback is turned on and causes the circuit to adapt and compensate for any long-term differences between the transistor characteristics of M1 and M2. The negative feedback is turned on by causing V12 to go low (e.g., 0 volts) and transistor M12 to be turned on. When M12 is turned on, the feedback voltage applied to the gate of M1 causes the currents I1 and I2 to be substantially equal. Assume that M3, M4, M6 and M7 are all made to the have the same geometry. Then, for I1 equal to I2, the current I2 is mirrored through M7 so a current equal to I2 is drawn from node A3. Concurrently, the current I1 is mirrored through M6 and M8 and then mirrored via M9 to produce a current equal to I1 flowing into node A3. For I1 equal to I2, the voltage at node A3 will be equal to approximately VDD/2. The voltage at node A3 is applied to the input of source follower stage M10 to produce a similar output at node A4. When M12 is turned on, the voltage at A4 is applied, via the conduction path of M12, to the gate of M1 and will tend to cause equal currents to flow through M1 and M2. The high degree of feedback when M12 is turned on ensures that any drift in M2 gets compensated (i.e., the effect of the drift is effectively cancelled). Thus, when the circuit is ready to be used to sense ("sniff") the presence of any vapors or chemicals, transistor M12 is turned off by the application of a high voltage (e.g., VDD) to the gate of M12. When that occurs, the circuit is biased at an optimal operating point to respond to signals resulting from odors being "puffed" (applied) to the sensing OFET M2.

When the circuit is about to sniff or is sniffing, the feedback loop is opened (i.e., M12 is turned off) and the circuit sits at its high-gain balanced midpoint, ready to amplify any odor-caused change in the current through M2. The voltage at A3 serves as the output of the circuit with changes in the voltage of A3 reflecting changes induced by the odor response of M2.

This is best illustrated as follows. When the circuit is ready to sniff the presence of an odor, the feedback loop is opened (i.e., transistor M12 is turned off). When the loop is opened, capacitor C1 is charged (and remains so for some time) to the voltage present at the output of the amplifier immediately before M12 was turned off. Thus, the gate voltage of M1 which represents one of the two inputs of the differential amplifier is held at a value representative of the gate voltage just before the feedback loop is opened. When the odor is applied, M2 responds and its conductivity is modified by the chemicals present in the air or vapor being "sniffed". If the conductivity of M2 is decreased by the "input signal" then the current I2 is decreased relative to the current I1 and the voltage at node A3 will rise sharply and quickly in response thereto. On the other hand, if the conductivity of M2 is increased by the "input signal" then the current I2 is increased relative to the current I1 and the voltage at node A3 will drop sharply and quickly in response thereto. In either case a good indication of the input signal condition will be produced at the output of the amplifier with the d.c. shift and drift substantially removed from the output signal.

FIG. 5 also shows a switching subcircuit formed by transistors M12, M13, and M14. The implementation of the low pass filter and the switching subcircuit are now briefly described. Transistor M12 implements a switch that is turned on when the voltage V12 is low. Normally, V12 is driven low when the circuit is not "sniffing" and is driven high when the circuit is "sniffing". The conduction channels of transistors M13 and M14 may be ratioed to have half the width (W) and the same length (L) as transistor M12. They help to alleviate charge injection problems caused by the switching voltage of M12. The charge injection is alleviated by having a signal complementary to V12 drive M13 and M14. The charge injection is dominated by the overlap capacitances of transistor M12; the overlap capacitances of shorted-and-ratioed transistors M13 and M14 match those at the source and drain ends of M12 and serve to cancel the effects of positive charge injection from M12 with negative charge injection from M13 and M14.

Figure 6:
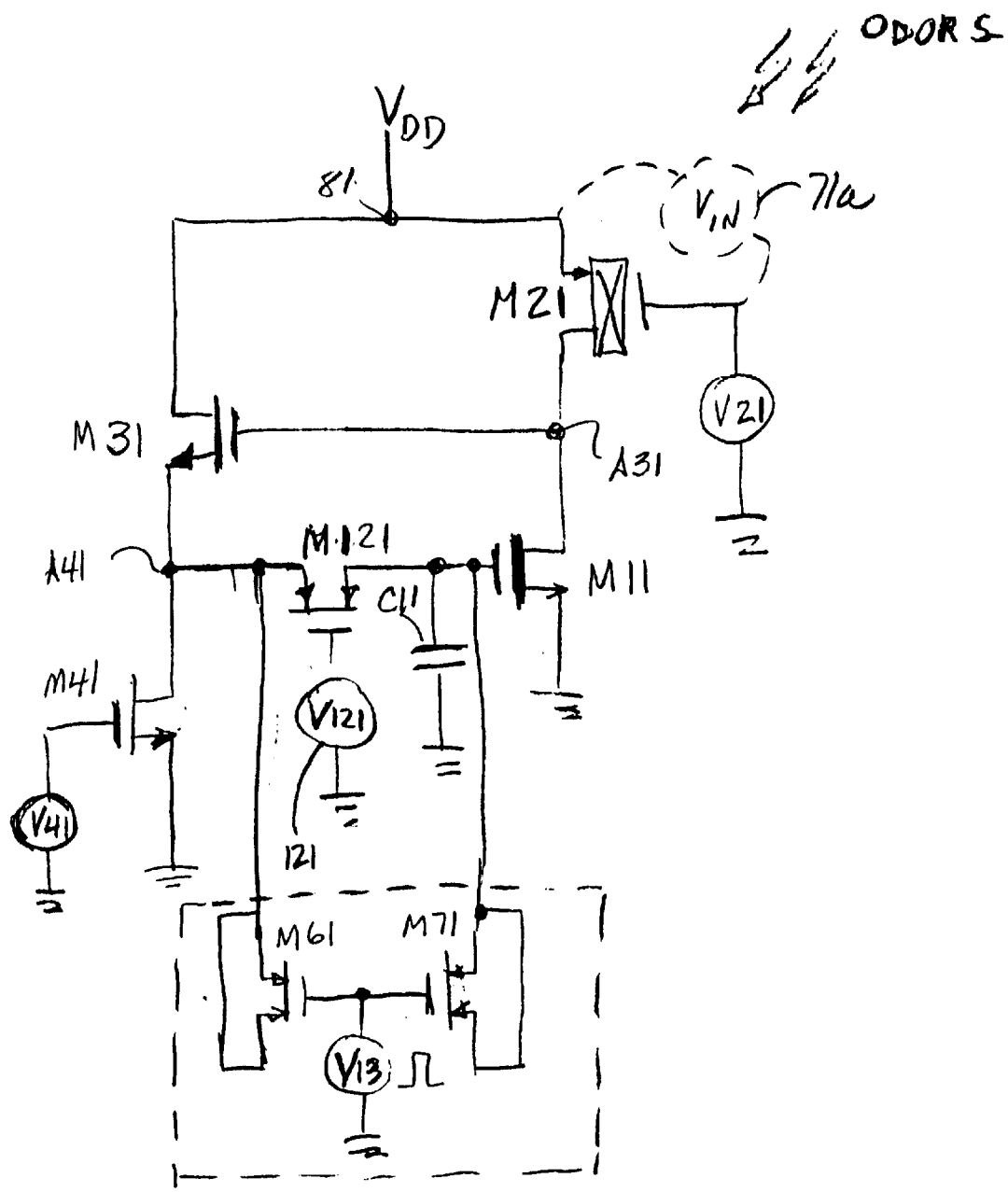
FIG. 6 is a schematic diagram of an OFET- amplifier combination embodiment.

FIG. 6 shows a circuit in which an odor responsive P-type OFET M21 is interconnected with a transistor M11 to form a common-source amplifier. The output (node A31) of the common-source amplifier is connected to the input of a source (voltage) follower stage comprised of transistors M31 and M41 whose output (node A41) is selectively fed back to the gate of M11 via transistor M121. As in FIG. 5, when odors/vapors are "puffed" onto OFET M21 the feedback loop is opened, and the common-source amplifier amplifies the signal due to the odors/vapors.

In FIG. 6, the source of M21 is connected to a power terminal 81 to which is applied VDD volts and its gate is connected to a constant bias voltage V21. The drain of M21 is connected to the drain of an N-type FET, M11, at output node A31. The source of M11 is connected to ground. Node A31 is connected to the gate of source follower transistor M31 whose drain is connected to terminal 81 and whose source is connected to terminal A41. Transistors M11 and M21 form a common-source amplifier with a control input being the gate voltage of M11 and a signal input being the current through M21 responsive to the odors/vapors puffed onto M21. The output of the common-source amplifier is the voltage at node A31. If the current through M21 exceeds the current through M11, then the node voltage A41 is driven near VDD. If, on the other hand, the current through M11 exceeds that through M21, the node voltage A41 is driven near ground. The output of the common-source amplifier is connected to the input of a source follower stage (the gate of M31) whose output (A41 at the source of M31) is fed back to the gate of M11 via switching transistor M121.

As in FIG. 5, an input signal source 71a is shown (with dashed lines) connected between the gate and source of M21 to indicate the signal input function of the sensor, internal to M21, when an odor/vapor is puffed onto M21. That is, signal source 71a represents the effect of a mobility or threshold change on and within transistor M21 when an odor is puffed onto it. Typically, the odor is puffed onto transistor M21 when the feedback loop is open (i.e., M121 is turned-off). Transistor M21 is the only odor sensitive transistor in the circuit; any other organic transistor in the circuit is assumed to be odor insensitive.

Transistors M31 and M41 form a standard N-type FET source follower stage whose bias current is set by a voltage V41 applied to the gate of M41. Transistor M121 is turned on when the circuit is not sniffing. When M121 is turned on the output of the source follower is tied to a capacitor C11 such that transistors M31, M41 and the capacitor C11 implement a weakly nonlinear low pass filter. The time constant of the low pass filter may be controlled by altering V41, the capacitance of C11, or both. Transistor M121 implements a switch that is turned on and off by a signal source 121 producing a voltage V121.

When the circuit is not sniffing, the source 121 applies a low voltage to the gate of M121 to enable the negative feedback loop and cause the voltage at A41 to be applied to capacitor C11 and the gate of M11. Thus, during the non-sensing mode, the gate of transistor M11 is connected to a low pass filtered version of the common-source amplifier's output in a negative feedback configuration. Consequently, during this mode, the gate voltage of M11 constantly adapts to compensate for long-term changes in the threshold or mobility of transistor M21 and keeps the output A31 of common-source amplifier (M11, M21) at its balanced equilibrium.

When the circuit is sniffing, the negative feedback is turned off and the circuit sits at its gain balanced equilibrium, ready to amplify any odor-caused change in the current through transistor M21. The output voltage at A31 reflects changes induced by the odor response of M21. When the circuit is not sniffing, the negative feedback is turned on and causes the circuit to adapt and compensate for any long-term changes in the characteristics of OFET transistor M21.

FIG. 6 also shows a switching sub-circuit formed by transistors M121, M61, and M71 which is active only when V121 is active low. The implementation of the lowpass filter and the switching subcircuit are now briefly described. Transistors M61 and M71 are ratioed to have half the W and the same L as transistor M121. They help to alleviate charge injection problems caused by the switching voltage of M121. The charge injection is alleviated by having a signal (V13) complementary to V121 drive M61 and M71. The charge injection is dominated by the overlap capacitances of transistor M121. The overlap capacitances of shorted-and-ratioed M61 and M71 match those at the source and drain ends of M121 and cancel charge injection from M121 with charge injection from M61 and M71.

Figure 7:
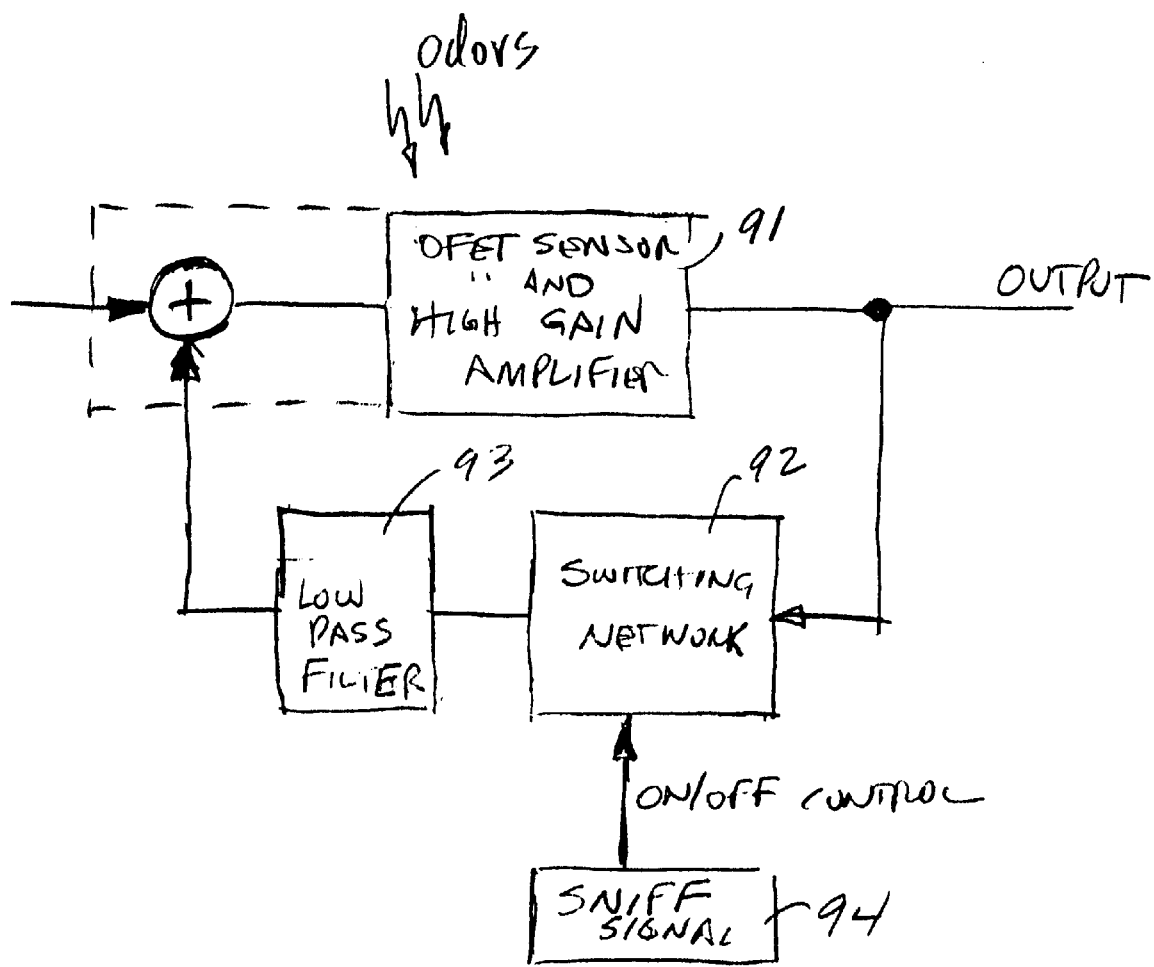
FIG. 7 is a block diagram of a system employing OFETs in one embodiment.

Features of the circuits of various embodiments, which were discussed above in FIGS. 5 and 6, are shown in FIG. 7. FIG. 7 includes a high gain amplifier 91 responsive to signals from an OFET sensor that is integral to one of the amplifying devices in amplifier 91. The output of the amplifier is selectively fed back by means of a switching network 92 and a low pass filter 93 to a control input of the amplifier 91. The switching network is turned on and off as a function of a sniff signal circuit 94 which controls the application of chemical odors/vapors/gases (analytes) to the sensor contained within the high gain amplifier. During a non-odor-sensing period of time, the switching network 92 closes the negative feedback loop such that the low pass filter 93 is coupled between the output of amplifier 91 and an input of amplifier 91. During an odor-sensing period of time, the switching network is open so that the feed back loop is removed from the circuit, and the high gain amplifier 91 amplifies signals resulting from the flow of odors over the OFET sensor.

Figures 1, 1A:
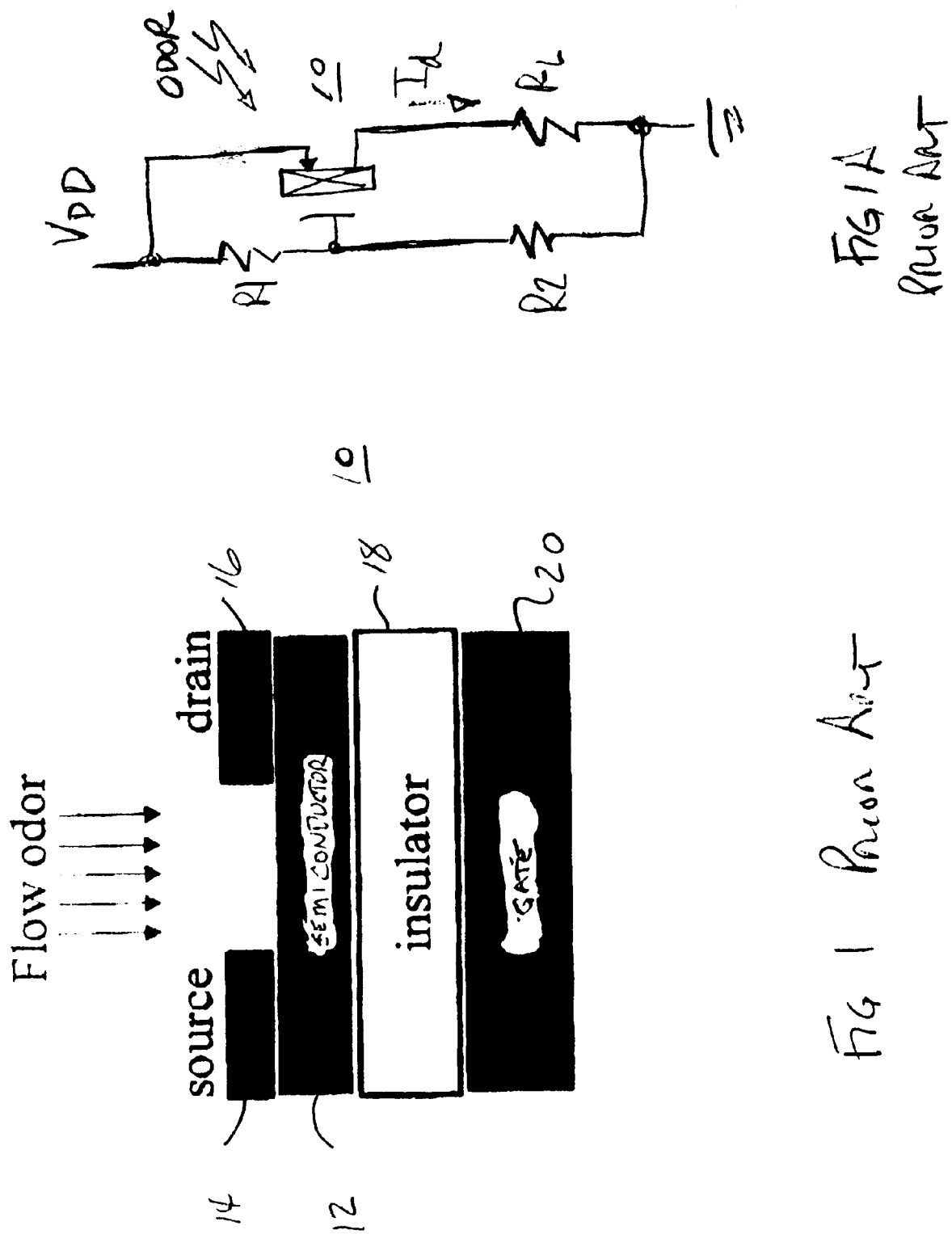
FIG. 1 is a highly simplified cross-section of a known OFET suitable for use in various embodiments.
FIG. 1A is a prior art circuit diagram of a discrete OFET circuit to sense and amplify signals resulting from odors.
Figure 2B:
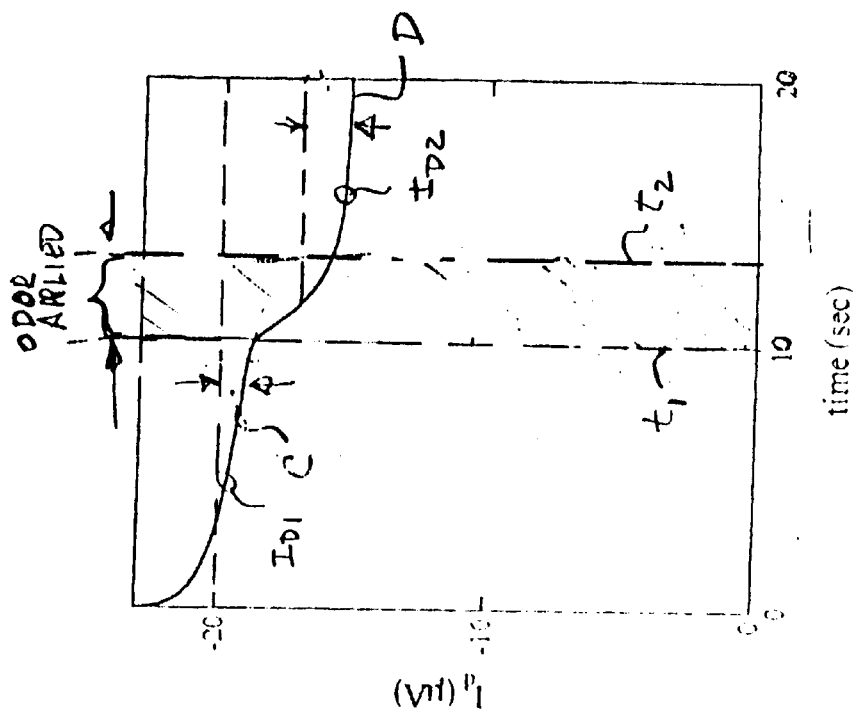
FIGS. 2A and 2B are diagrams illustrating the drift in the current through the conduction path of an OFET as a function of time.
Figure 2A:
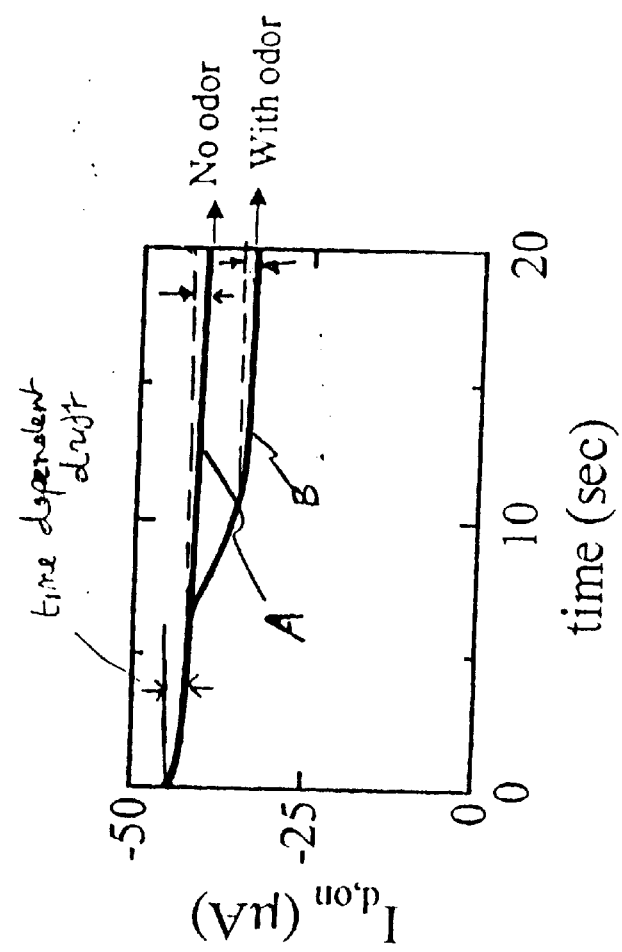

To better explain other embodiments, assume, as shown in FIGS. 1A and 2B, that a discrete OFET is biased to conduct a source-drain current having a value $I_{D1}$ prior to any odor being applied to the OFET, When an odor is "puffed" onto the OFET, the source-drain current changes from $I_{D1}$ to $I_{D2}$ in response to an odor (analyte) incident on the OFET from a time I1 to a time I2. Thus, after an odor signal is applied to an OFET, the source-to-drain current changes. The change in the source-to-drain current persists even after the removal of the odor. When an odor is applied for a given time (e.g., 5 seconds), it normally takes a much longer period of time (e.g., one minute) for the OFET current to recover from the value of $I_{D2}$ to a value approximately equal to that of $I_{D1}$.

After an OFET is subjected to an odor signal, applying an electrical bias cycle to the gate of an OFET facilitates its recovery to the condition existing prior to the application of the odor. That is, by applying an electrical signal to the gate of the OFET which goes positive and negative (or negative and positive) relative to the source (and/or drain) of the OFET, the OFET recovers more quickly and the degree of recovery is enhanced. Full recovery means the return of the drain current of the OFET to the level it would have had had an odor signal not been applied to the OFET.

In various embodiments, OFETs are operated so that they return more quickly to the existing operating condition extent immediately before the application of the selected odor (analyte) to the circuit. Ring oscillators employing OFETs to sense the presence of odors are very useful as sensing circuits for selected odors.

Ring Oscillator Sensors

Figure 8:
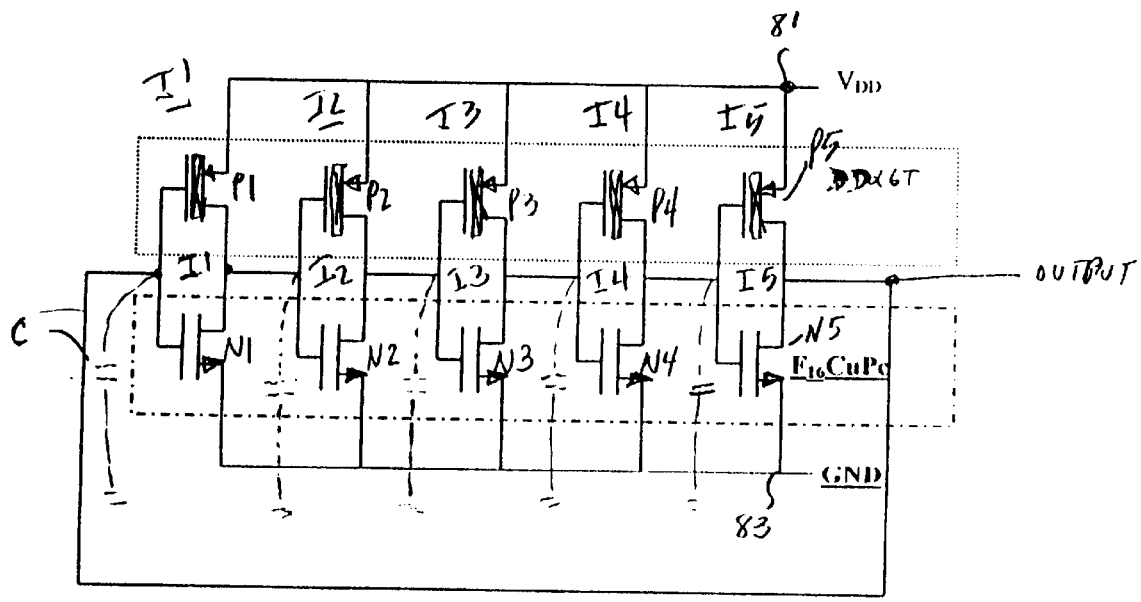
FIG. 8 is a schematic diagram of a ring oscillator circuit employing OFETs in one embodiment.

Using OFETs in a ring oscillator circuit eliminates many of the above-discussed problems associated with OFETs. Referring to FIG. 8 there is shown five complementary inverters (I1–I5) interconnected to form a ring oscillator. In FIG. 8 each inverter (I1–I5) includes a P-type OFET (P1–P5) and an N-type FET (N1–N5). In one embodiment of the FIG. 8 circuit, the P-type OFETs were made of didodecyl α-sexithiophene (DDα6T) material and the N-type FETs were made of hexadecafluoro copper phthallocyanine ($F_{16}$CuPc) material. In that embodiment, the material DDα6T was used to form the P-type OFETs because DDα6T is sensitive to the analyte octanol and esters such as allyl propionate which are the analytes selected to be sensed by the circuit. In contrast, the material $F_{16}CuPc$ was used to make the N-type OFETs, because it is insensitive to octanol and esters such as allyl propionate. Therefore, the N-type OFETs (N1–N5) are insensitive or, at least, less sensitive to the selected analytes and could be replaced by standard N-type FETs.

The source electrodes of the P-type transistors (P1–P5) are connected to a power terminal 81 to which is applied +VDD volts. The source electrodes of the N-type FETS (N1–N5) are connected to a power terminal 83 to which is applied ground potential. The gate electrodes of the two transistors forming each inverter are connected in common and define a signal input terminal to the inverter. The drain electrodes of the two transistors forming each inverter are connected in common and define a signal output terminal of the inverter. Starting with the first inverter, the output of each inverter along the chain is connected to the input of the next inverter along the chain, except for the output of the last inverter (e.g., I5) which is fed back to the input of the first inverter. Note that there is some capacitance, C, (which may be parasitic or discrete) associated with the input (gates) of each inverter. The combination of the effective output impedance of each inverter and the input capacitance of the next stage determines the time constants of each stage and the frequency of oscillation of the circuit.

In one embodiment, the oscillation frequency of the 5-stage all organic $F_{16}CuPc/DD\alpha 6T$ complementary ring oscillators ranged from a few Hz to several kHz. A selected analyte was "puffed" onto the ring oscillator circuit. The analyte reduced the conductivity of the P-type OFETs. In the discussion to follow, it is assumed that the conductivity of the OFET decreases when subjected to a gas (analyte). However, it should be understood that other OFETs have conductivities that increase when subjected to an odor (analyte). For OFETs whose conductivity increases in response to the presence of an odor, the circuit configurations discussed are also suitable. However, the response of the circuit would be the inverse of that described below (i.e., the frequency of oscillation would increase rather than decrease).

Figure 9:
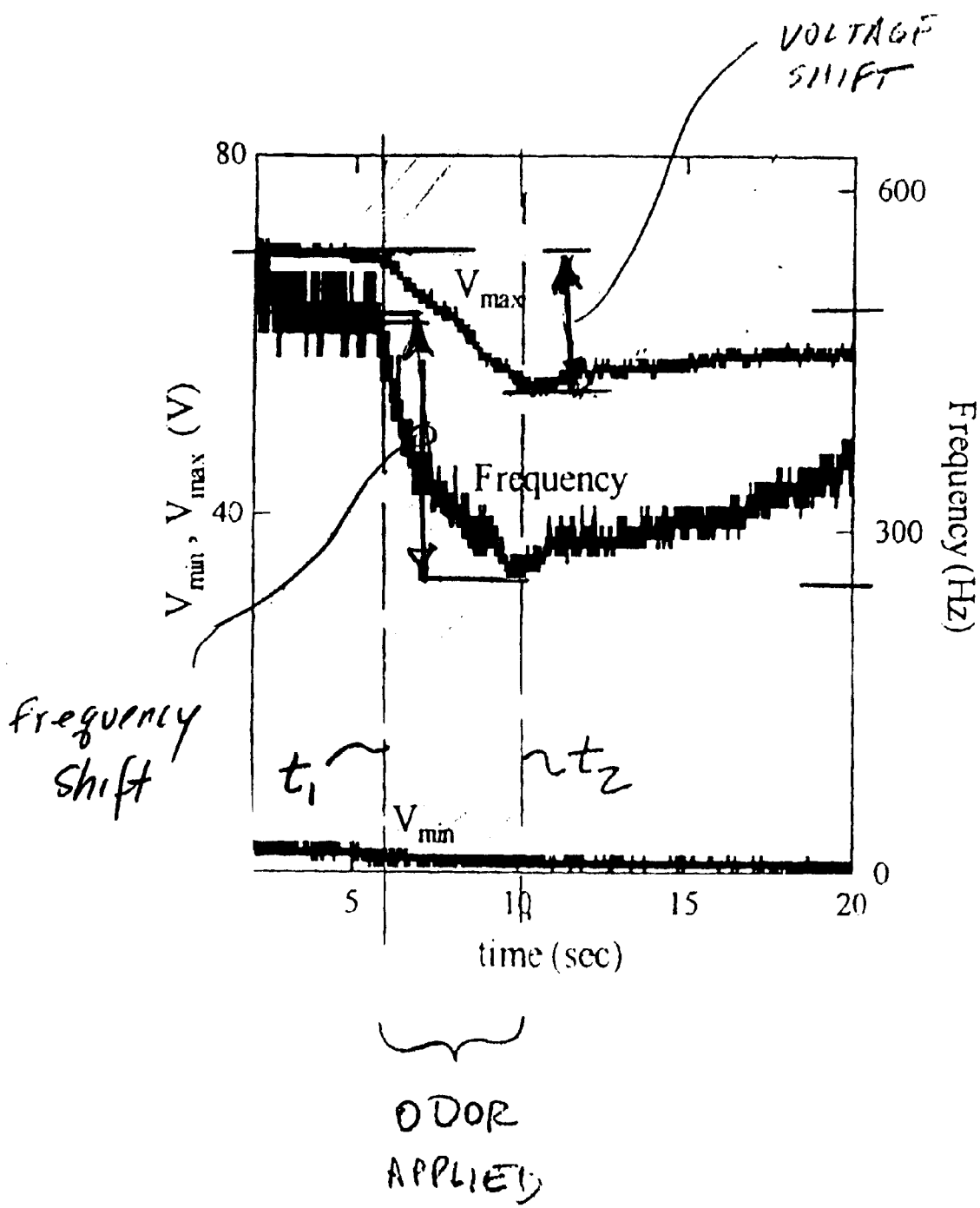
FIG. 9 is a diagram of waveforms associated with one embodiment of the circuit of FIG. 8.

The mobility of the discrete $F_{16}CuPc$ transistors and of the DDα6T transistors, measured on devices fabricated alongside the ring oscillators, was approximately equal to $\sim 10^{-2}$ $cm^2/V\text{-s}$. The response of the circuit was measured with an oscilloscope with a high input impedance (50 M ohm) probe. The response of a particular circuit configured as illustrated in FIG. 8 is shown in FIG. 9. The change in frequency as a consequence of the odor is clearly seen. Due to the decrease in the conductivity of the P-type OFETs, there is an increase in the RC time constants of the inverting stages. This causes the oscillation frequency to decrease very sharply. Note that FIG. 9 depicts the response of the circuit of FIG. 8 to an analyte "puffed" onto the circuit from time t1 to time t2 (approximately 5 seconds). As a result of the incident odor "puffed" onto the circuit the frequency changed from around 550 Hz to around 280 Hz. Thus a frequency change of nearly 50% was observed. A change in the amplitude of the oscillations was also observed (i.e., change in Vmax). The observed change is also much greater than the change observed in a discrete OFET in response to the same odor intensity. This demonstrates that a circuit of the type shown in FIG. 8 is a better odor/gas sensor than using a circuit using a single OFET.

Referring to FIG. 9, it is also seen that beginning at time t2, after the odor (analyte) is no longer applied to the circuit, the circuit begins to return to its condition prior to application of the odor (analyte). Applying an alternating signal to the gate of an OFET having a polarity to turn-it-on harder for a first time period and then having a polarity to turn-it-off for a second period of time, tends to enhance the recovery of the OFET to the state it had prior to the application of an analyte. This is in sharp contrast to the response of the discrete OFET shown in FIG. 2B, where the response of the discrete OFET does not begin to recover immediately after removal of the odor (analyte).

When the ring oscillator circuit of FIG. 8 is exposed to a selected analyte, the mobility of the material (DDα6T) is changed and the oscillation frequency changes. This provides a convenient means of measuring the presence and concentration of the analyte. By making the OFETs sensitive to certain particular analytes and not to others it is also possible to ascertain the presence of these certain analytes. However, usually odorant detection will be done by pattern recognition based upon the responses of several sensors. Therefore, it is generally not necessary to have sensors that respond only to a particular odorant.

Figure 10:
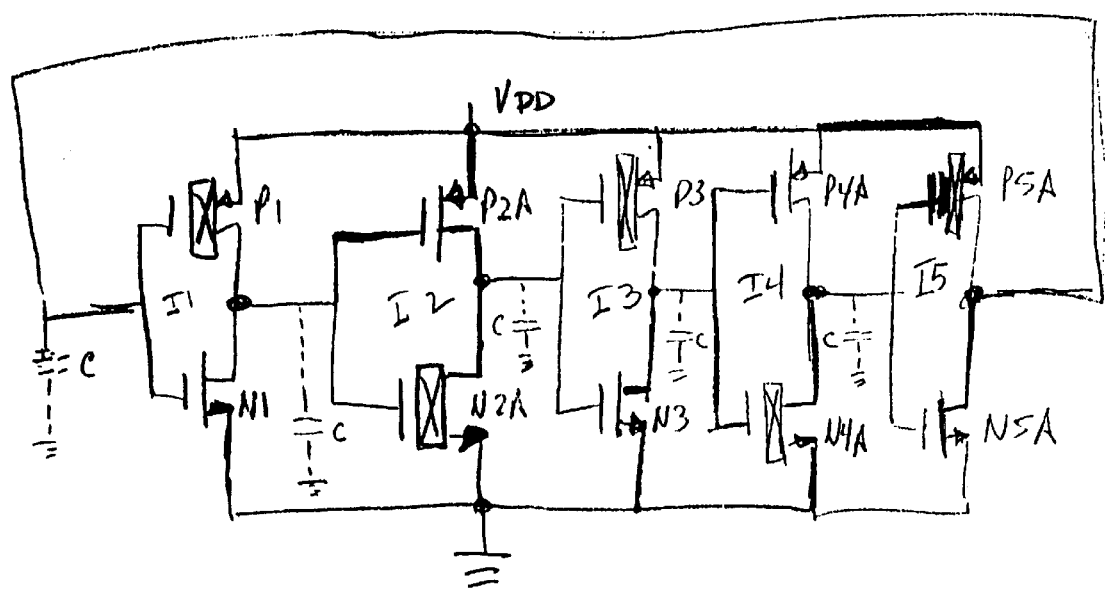
FIG. 10 is a schematic diagram of another ring oscillator circuit employing OFETs in one embodiment.

In the circuit of FIG. 8 the P-type transistors P1–P5 are OFETs formed on an integrated circuit (IC) by similar masking and processing steps. It is possible to obtain a still higher gain response by using OFETs of complementary conductivity as shown in FIG. 10. FIG. 10 is another embodiment of an oscillator circuit in which complementary inverters are arranged such that in every other inverter (e.g., the odd numbered inverters) the P-type transistor is an odor-sensitive OFET and in the intermediate inverters the N-type transistor is an odor-sensitive OFET. The OFETs in the circuit of FIG. 10 are formed of materials which cause their conductivity to decrease when a selected analyte is puffed on the OFETs. Consequently, when an analyte is applied to the ring oscillator circuit of FIG. 10, the conductivity of OFETs P1, P3 and P5A and OFETs N2A and N4A decreases. Therefore, each cascaded inverter is responsive to the presence of the analyte. In addition, the output of each inverter (e.g., I1) is applied to the input of the next inverter (e.g., I2) along the chain with a phasal relationship that results in the further amplification by the next inverter (e.g., I2) of the signal from the preceding stage (e.g., I1). For example, beginning with inverter I1, in response to an odor signal, the output of inverter I1 produces a signal which is an amplified version of the response of OFET P1. Since the conductivity of P1 decreases, in response to the odor, the effective impedance of P1 increases and the current through P1 decreases resulting in more time being required to charge the capacitance at the output node of inverter I1. The output of I1 is applied to the input of inverter I2. By making N2 an OFET whose conductivity also decreases (i.e., its effective impedance increases) in a similar manner to that of OFET P1, inverter I2 functions to further amplify the response at the output of I1. This is evident from noting that as the effective impedance of OFET N2 increases it causes the voltage at the output of I2 to be discharged more slowly and hence the output of I2 to decrease more slowly from its high state. Concurrently, the decrease in the voltage at the output of I1 applied to the gate of N2 also causes N2 to conduct less. Hence, the condition at the output of I2 is reinforced by the signal at the output of I1. In a similar manner to that just described, making P3 an OFET and N3 a regular FET ensures that the signals from the previous stages is amplified in phase with the signal generated by P3 in response to its sensing an analyte. This same amplification of the sensed signal within a stage in cascade with the amplified signals of the previous stages occurs in inverter I4.

Different forms of the cascaded inverting stages using OFETs to sense odors of the type shown in FIGS. 8 and 10 may be used to practice the invention. An embodiment shown in FIG. 10A includes a first inverting stage comprising a P-type OFET, T1, and an odor-insensitive FET, T2. The source electrode of T1 is connected to power terminal 81 to which is applied VDD volts and its drain electrode is connected to node 101. A bias voltage VB is applied to the gate of T1 to bias T1 at a desired operating point. T2 is shown as an N-type FET, but it may be a P-type FET or any load device. A control voltage, VC1, is applied to the gate of T2 to control the conductivity of T2 independently of the bias voltage applied to T1. The drains of T1 and T2 are connected in common at node 101 at which is produced the output of the first inverting stage. The source of T2 is returned to ground potential. The second inverting stage includes a P-type OFET, T3, having its gate electrode connected to node 101, its source electrode connected to node 81 and its drain connected to node 103. A load, shown as a resistor RL, but which, in practice, may be a passive or active load, is connected between node 103 and ground potential. The signal generated at node 103 may be supplied to any suitable signal amplifying or processing circuit.

Figure 10A:
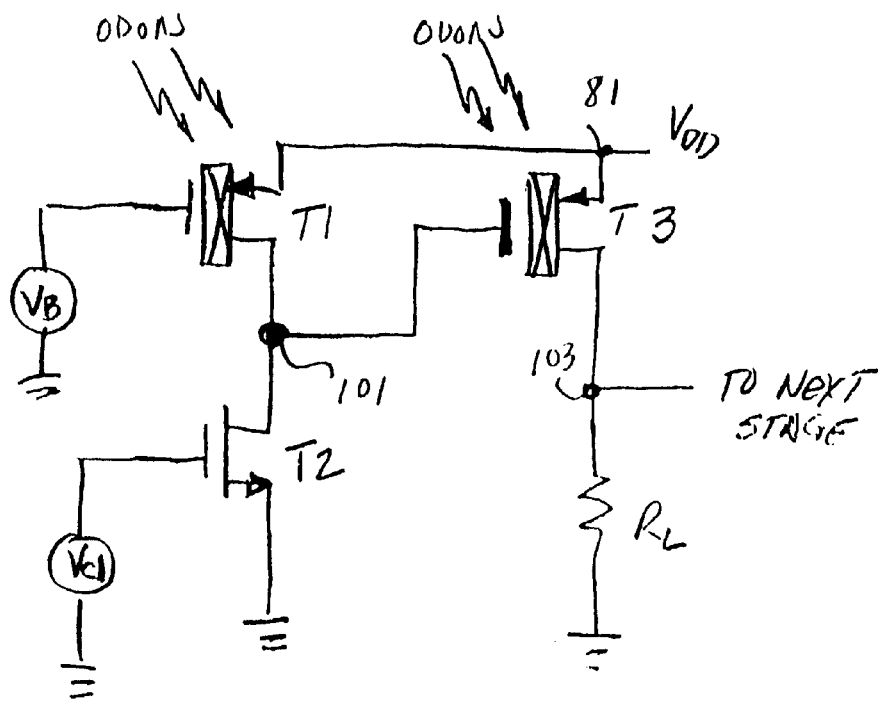
FIGS. 10A and 10B are schematic diagrams of cascaded inverters using OFETs for analyte sensing.
Figure 10B:
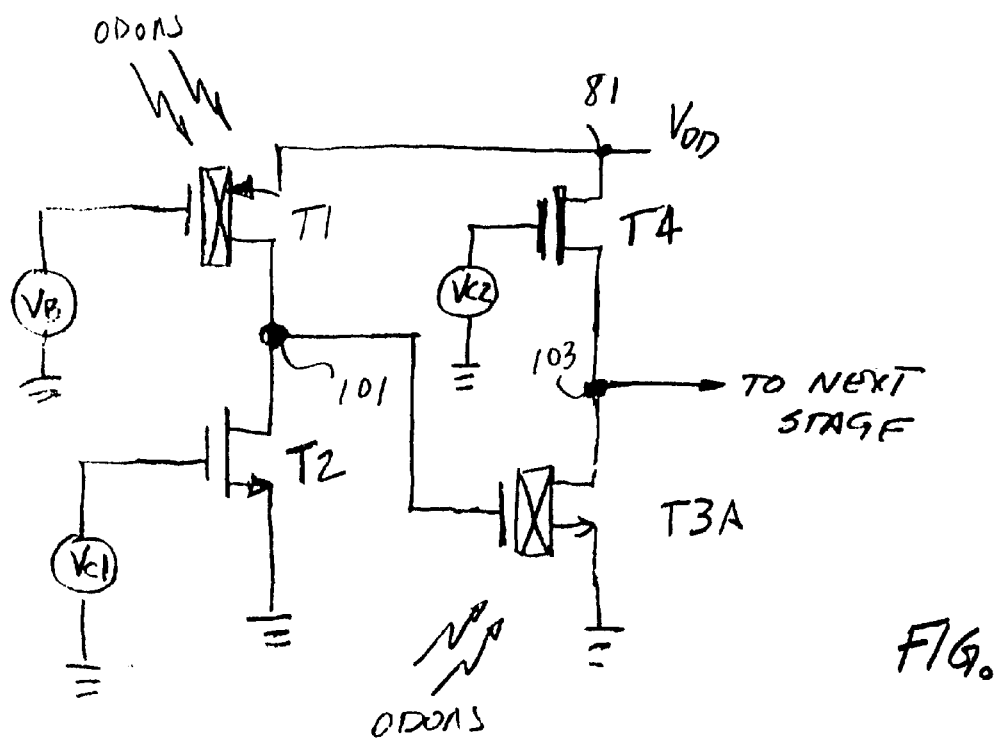

Another embodiment is shown in FIG. 10B. the first inverting stage is similar to that of FIG. 10A. However, the second inverting stage includes an N-type OFET T3A connected at its gate electrode to node 101, at its source electrode to ground potential and at its drain electrode to output node 103. A fourth transistor T4 has its source-to-drain path connected between terminal 81 and node 103. the gate electrode of T4 is shown connected to a control voltage source VC2 designed to control the conductivity (impedance) of T4. T4 may be an active load (e.g., an N-FET, a P-FET, or an OFET) or it maybe replaced by a passive resistive load.

In FIGS. 10A and 10B, the inverting stages are cascaded to enhance signal amplification and increase the sensitivity of the odor sensitive transistors to the application of analytes (odors). The circuits of FIGS. 8, 10, 10A and 10B illustrate the use of multiple sensors (two, or more OFETs) that are connected in circuit to coherently amplify the effects of an analyte by acting synchronously. Thus, small changes produced in a single stage in response to a weak analyte concentration applied to the circuit are amplified over several stages leading to an improvement in signal to noise.

Figure 11:
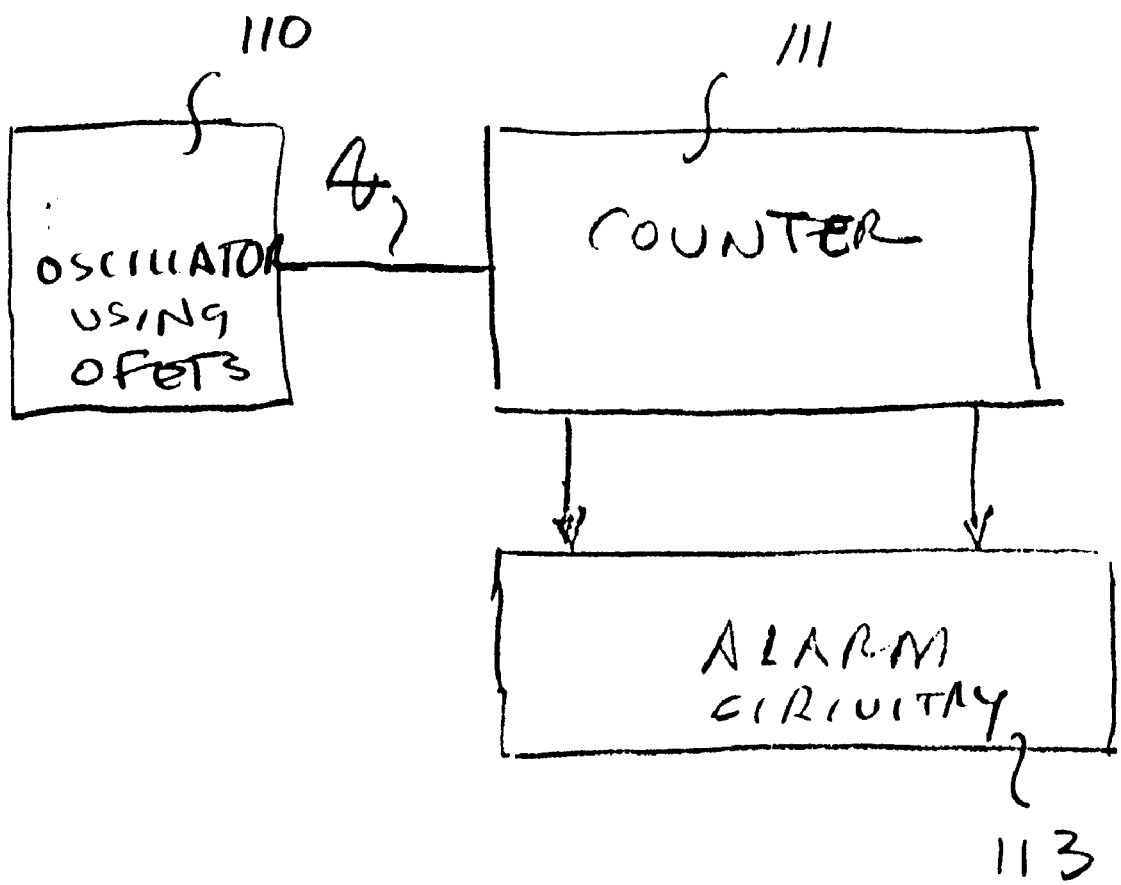
FIG. 11 is a block diagram of an odor sensor in one embodiment.
Figure 18:
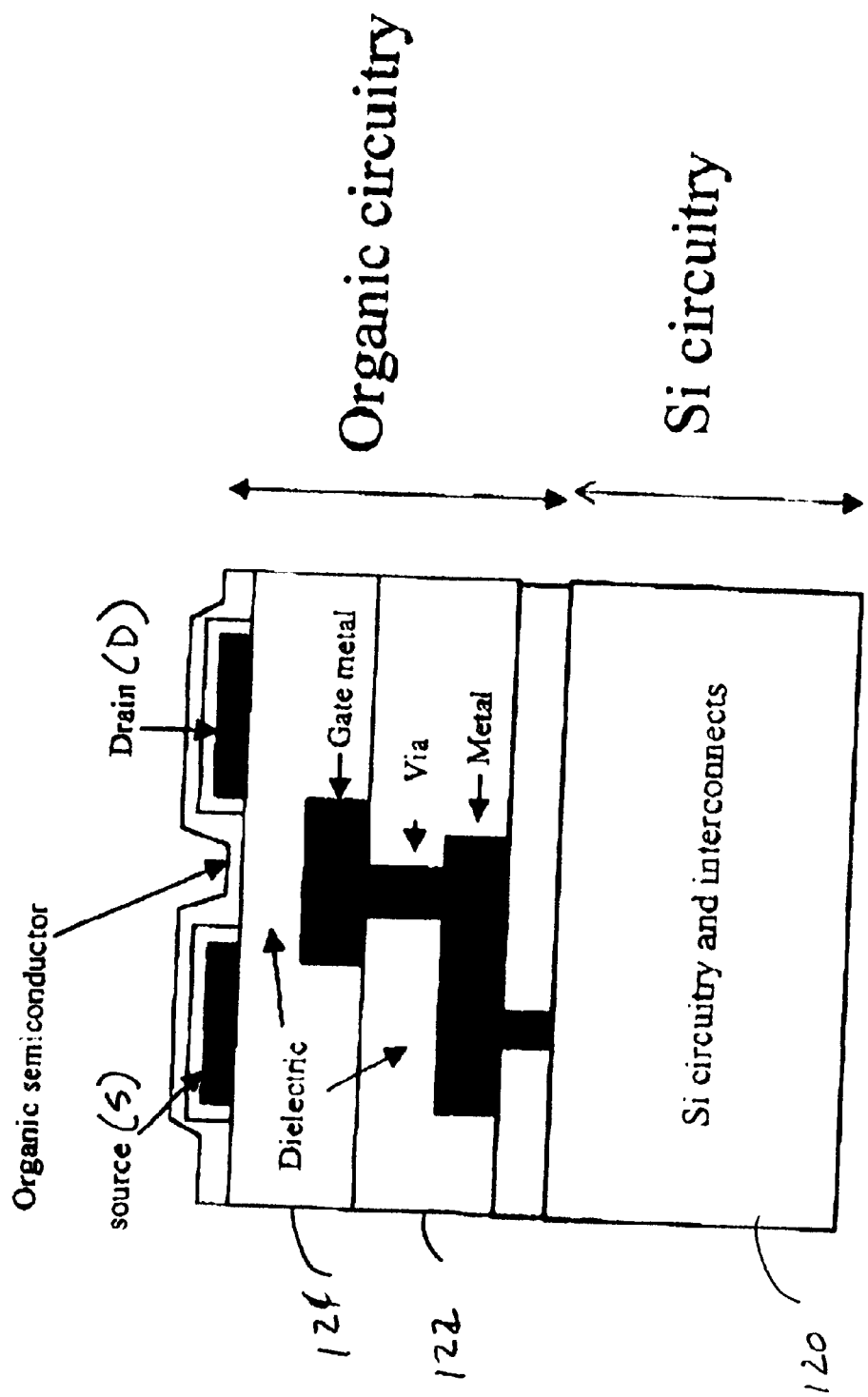

Referring to FIG. 11, there is shown an oscillator 110 coupled to a counter circuit 111 whose outputs are coupled to an alarm circuit 113. The oscillator 110 may be any suitable oscillator using at least one odor-sensitive OFET for varying the frequency of oscillation in response to a selected odor. By way of example, oscillator 110 may be a ring oscillator as shown in FIGS. 8 and 10. Any suitable output signal of the oscillator can be applied to a counter 111 that tracks and calculates frequency of oscillations. If the frequency decreases below a predetermined level, for the condition where the response of the OFET to a selected odor causes the oscillator to decrease, the output of the counter 111 activates processing circuitry 113 and activates an alarm. Alternatively, if the frequency increases above a predetermined level, for a condition when the response of the OFET to a selected odor causes the oscillation to increase., the output of the counter 111 activates processing circuitry 113 and activates an alarm.

OFETS for use in circuits embodying the invention may be formed as shown in FIG. 12. Note that a substrate 120 of standard Si electronics (both FET and bipolar) fabricated in a conventional manner known in the art as integrated circuit (IC) fabrication may be used. After the fabrication of the different levels of metallization needed for the Si circuitry, organic transistor sensor circuits are fabricated employing an upside-down approach. In the upside down approach, OFET circuits are formed by sequentially defining the interconnects, the gate metal level, a dielectric layer, source-drain metal level and the organic semiconductor layer. The organic semiconductor sees minimal post-deposition processing. The approach of FIG. 12 is different from typical circuit fabrication procedures where the transistor devices are first formed followed by the interconnections. However, any suitable fabrication scheme may be used to form circuits embodying the invention.

In FIG. 12, the fabrication of the organic FET circuits begins with the deposition (above the silicon circuitry) of a thick layer (122, 124) of $SiO_2$ (for isolation). The metal lines and vias (through-holes for the metal interconnects) are defined by photolithography and standard semiconductor processing techniques. The interconnection metal (Al) level is defined immediately above the substrate followed by the gate metal level (Al) and the source/drain metal level. The gate dielectric 124 may be a bilayer consisting of 20 nm of $Si_3N_4$ and 10 nm of $SiO_2$, with a capacitance of 200 $nF/cm^2$. The interlayer isolation dielectrics 122 are $SiO_2$ or $Si_3N_4$. The organic semiconductors are deposited as a thin layer above and between the source (S) and drain (D) contacts. The S/D contacts are coated with a gold layer by electroless/immersion techniques to facilitate good ohmic contact with the organic semiconductors. The underlying Si electronics and the above-lying organic circuitry are electrically interconnected as required through dielectrics by forming vias. The organic transistor circuitry may include any combination of the circuits described above. The active organic semiconductor material is deposited over the pre-formed source-drain contacts and gate insulator may be any suitable material for the desired sensor selectivity.

The molecular structures of some materials used to form OFETs are shown in FIG. 13. Exemplary materials for active semiconductor layers of P-type OFETs include:
 a. didodecyl α-sexithiophene (DDα6T);
 b. dioctadecyl α-sexithiophene;
 c. copperphthallocyanine;
 d. α-sexithiophene;
 e. α,ω-dihexylsexithiophene;
 f. poly(3-alkythiophene);
 g. poly(3-hexylthiophene); and
 h. poly(3-dodecylthiophene).
Exemplary materials for active semiconductor layers of N-type OFETs include:
 a. hexadecafluorocopperphthallocyanine ($F_{16}CuPc$); and
 b. naphthalenetetracarboxylic diimide compounds.

These materials are listed by way of example only and any other suitable materials may be used.

Figure 14:
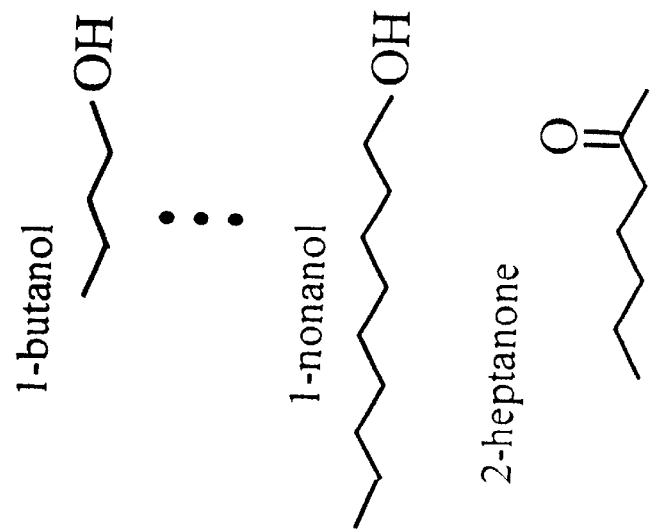
FIG. 14 is a drawing of examples of molecular structures of odors to be sensed by circuits of various embodiments.

The molecular structures of some odors used to test circuits embodying the invention are shown in FIG. 14. However, it should be understood that any gas, chemical vapor, odor or analyte which causes a change in the conductivity of an OFET may be sensed by circuits embodying the invention.

The various embodiments shown herein are for purpose of illustration, and the invention may be practiced using any suitable circuit.

What is claimed is:
1. An analyte sensor comprising:
 a series of N inverters, where N is an odd integer greater than 1, each inverter having a signal input terminal and a signal output terminal and including a first transistor with source, drain and gate electrodes, the gate electrode being connected to the signal input terminal of the corresponding inverter and the drain electrode being connected to the signal output terminal of the corresponding inverter;

wherein at least one of the first transistors is an organic transistor having a conduction path whose conductivity is responsive to presence of an odor with the signal output terminal of each inverter being connected to the signal input terminal of the next inverter in the series.

2. The analyte sensor of claim 1, wherein the signal output terminal of the last inverter of the series and the signal input terminal of the first inverter of the series are connected to form a ring oscillator.

3. An analyte sensor as claimed in claim 2, wherein each one of said first transistors is an organic field effect transistor (OFET) having a conduction path whose conductivity changes in response to the selected odor incident on said first transistors.

4. An odor sensor as claimed in claim 3, wherein the first transistors of every other inverter are of a first conductivity type and the first transistors of the remaining inverters are of a second conductivity type complementary to said first conductivity type.

5. An analyte sensor as claimed in claim 2, wherein each one of said N inverters includes a second transistor; wherein one of said first and second transistors of each inverter is an odor sensitive organic transistor and the other one of said first and second transistors is odor insensitive.

6. An analyte sensor as claimed in claim 2, wherein each one of said N inverters includes a second transistor; wherein one of said first and second transistors of each inverter is an odor sensitive organic field effect transistor (OFET) and the other one of said first and second transistors is odor insensitive field effect transistor (FET).

7. An analyte sensor as claimed in claim 2, wherein each one of said N inverters includes a second transistor; wherein one of said first and second transistors of each inverter is an odor sensitive organic transistor and the other one of said first and second transistors is an odor insensitive organic transistor.

8. An analyte sensor as claimed in claim 3, wherein said organic field effect transistor has a semiconductor channel formed from one of the following materials: (a) didodecyl α-sexithiophene (DD α6T); (b) dioctadecyl α-sexithiophene; (c) copperphthallocyanine; (d) α-sexithiophene; (e) α,ω-dihexylsexithiophene; (f) poly(3-alkythiophene); (g) poly(3-hexylthiophene); (h) poly(3-dodecylthiophene); (i) hexadecafluorocopperrphthallocyanine (F 16CuPc); and (j) naphthalenetetracarboxylic diimide compounds.

9. The analyte sensor as claimed in claim 5, wherein one of said first and second transistors has a conductivity that decreases when subjected to the presence of the analyte.

10. The analyte sensor of claim 2, wherein the frequency of oscillation of the ring oscillator decreases when the ring oscillator is subjected to the analyte.

11. A gas sensor comprising:

N inverters, where N is an odd integer greater than 1, wherein each one of said inverters has a signal input terminal and a signal output terminal; each inverter having a first transistor of first conductivity and a second transistor of a complementary conductivity type; the first and second transistors of each inverter being interconnected to form an inverter, one of the first and second transistors of one of the inverters being an organic transistor which is responsive to an analyte; and the N inverters being connected in a cascade, with the signal output terminal of the last inverter of the cascade being connected to the signal input terminal of the first inverter of the cascade to form a ring oscillator.

12. A gas sensor as claimed in claim 11, wherein said transistors are field effect transistors (FETs) and wherein each organic transistor is an organic field effect transistor (OFET).

13. The sensor of claim 11, wherein the first and second transistors are organic field effect transistors with different sensitivities to the analyte.

14. The sensor of claim 11, wherein the analyte is one of an odor, a chemical and a vapor.

15. A gas sensor as claimed in claim 13, wherein the first transistors have active channels formed from one of the following materials:

a. didodecyl α-sexithiophene (DDα6T);
b. dioctadecyl α-sexithiophene
c. copperphthallocyanine;
d. α-sexithiophene;
e. α,ω-dihexylsexithiophene;
f. poly(3-alkythiophene);
g. poly(3-hexylthiophene); and
h. poly(3-dodecylthiophene);

and wherein the second transistors have active channels formed from one of the following materials:

hexadecafluorocopperphthallocyanine ($F_{16}CuPc$); and
naphthalenetetracarboxylic diimide compounds.

16. An apparatus comprising:

an odor-sensitive organic transistor having a semiconductor channel exposed to ambient odors; and an odor-insensitive organic transistor having a semiconductor channel protected from ambient odors, the two transistors being interconnected together to generate an output signal dependent on currents flowing through the two transistors and on whether an ambient odor is present.

17. An apparatus as claimed in claim 16 wherein the two transistors are of complementary conductivity type and are interconnected to form a complementary inverter.

18. An apparatus as claimed in claim 17 wherein the output signal is generated by the inverter and the inverter has a switching point dependent on both transistors and on whether the odor is present.

19. A gas sensor comprising:

a ring oscillator including at least one organic field effect transistor (OFET), the ring oscillator having frequency of oscillation that is a function of whether at least one of selected odors is present; and a circuit responsive to the frequency of oscillation of the ring oscillator and configured to provide an indication of when the oscillations of the oscillator are within or outside a predetermined range.

20. The sensor of claim 19, wherein the oscillator is a cascaded chain of inverters, the inverters including odor-sensitive organic transistors.

21. An odor sensing circuit including:

an organic field effect transistor (OFET) having source and drain electrodes defining the ends of a conduction path and a gate electrode; the conductivity of the conduction path of said OFET changing in response to selected odors incident on the OFET and in response to the value of voltages applied to the gate electrode;

circuitry for biasing the OFET so it is responsive to the application of odors; and circuitry for applying an alternating signal to the gate of the OFET for enhancing its recovery to the condition existing prior to the application of any odors.

22. An analyte sensor comprising: first and second power terminals for the application of an operating potential therebetween;

first and second organic field effect transistors (OFETs) responsive to the presence of an analyte, each one of said OFETs having source, drain and gate electrodes;

the source and drain of the first OFET being connected between said first power terminal and a first node;

the gate electrode of the second OFET being connected to the first node; and the source and drain of the second OFET being connected between a second node for producing thereat a signal indicative of the presence of said analyte and one of said first and second power terminals.

23. An analyte sensor as claimed in claim 22, wherein said first and second OFETs are of the same conductivity type and wherein the source of the second OFET is connected to said first power terminal.

24. An analyte sensor as claimed in claim 23 wherein a bias voltage is applied to said first OFET.

25. An analyte sensor as claimed in claim 24, wherein a third transistor is connected between said first node and the second power terminal, and wherein an output load is connected to the second node.

26. An analyte sensor as claimed in claim 22, wherein said first and second OFETs are of complementary conductivity type and wherein the source of the second OFET is connected to said second power terminal.

27. An analyte sensor as claimed in claim 26, wherein a bias voltage is applied to said first OFET; and wherein a third transistor is connected between said first node and said second power terminal and a fourth transistor is connected between the second node and the first power terminal.

* * * * *